Figure 1A:
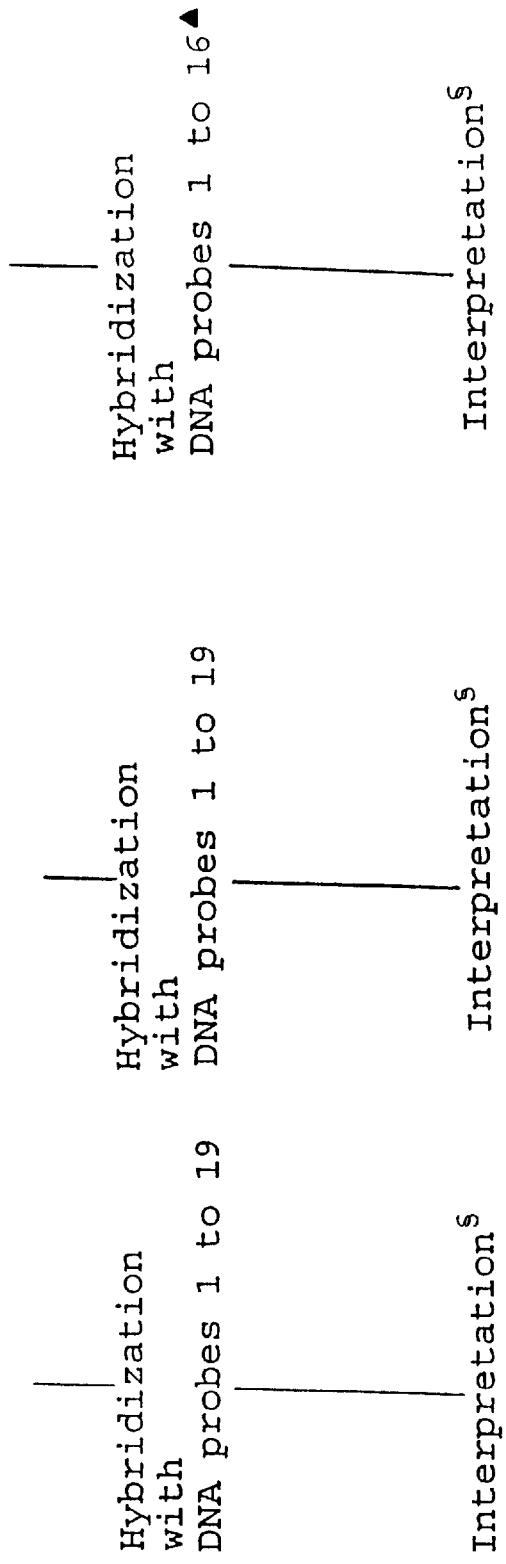

United States Patent [19]
Andrien et al.

[11] Patent Number: 5,883,238
[45] Date of Patent: Mar. 16, 1999

[54] PROCESS FOR TYPING HLA-B USING SPECIFIC PRIMERS AND PROBES SETS

[75] Inventors: Marc Andrien; Etienne Dupont, both of Brussels; Rudi Rossau, Ekeren; Ilse De Canck, Antwerp, all of Belgium

[73] Assignee: N.V. Innogenetics S.A., Ghent, Belgium

[21] Appl. No.: 532,727

[22] PCT Filed: Mar. 7, 1994

[86] PCT No.: PCT/EP94/00654

§ 371 Date: Oct. 23, 1995

§ 102(e) Date: Oct. 23, 1995

[87] PCT Pub. No.: WO94/21818

PCT Pub. Date: Sep. 29, 1994

[30] Foreign Application Priority Data

Mar. 18, 1993 [EP] European Pat. Off. ............. 93400700

[51] Int. Cl.$^6$ .................... C07H 21/02; C07H 21/04; C12Q 1/68
[52] U.S. Cl. ............ 536/23.1; 536/24.3; 435/6
[58] Field of Search ................ 435/6; 536/23.1, 536/24.3

[56] References Cited

U.S. PATENT DOCUMENTS

| 4,835,098 | 5/1989 | Orr et al. ..................................... 435/6 |
| 5,525,492 | 6/1996 | Hill et al. ................................. 435/91.2 |
| 5,550,039 | 8/1996 | Trachtenberg et al. ................. 435/91.2 |

FOREIGN PATENT DOCUMENTS

| 0354580 | 2/1990 | European Pat. Off. . |
| 0443748 | 8/1991 | European Pat. Off. . |
| 0540997 | 5/1993 | European Pat. Off. . |
| 9207956 | 5/1992 | WIPO . |

OTHER PUBLICATIONS

Yoshida et al, *Human Immunology*, vol. 34, 1992, pp. 257–266 "Polymerase–chain–reaction–based analysis of polymorphism in the HLA–B gene".

Hill et al, *The Lancet*, vol. 337, No. 8742, Mar. 16, 1991, pp. 640–642 "HLA class I typing by PCR: HLA–B27 . . . ".

Zemmour et al, *Tissue Antigens*, vol. 40, 1992, pp. 221–228 "HLA class I nucleotide sequences, 1992".

Staunton et al. Cell 52:pp 925–933 (1988).

Kawasaki et al., Methods in Enzymology 218: 369–381 (1993).

Bugawan et al., Immunogenetics 32:231–241 (1990).

The Stratagene Catalog, p. 39 (1988 Edition).

Eliaou et al., Human Immunology 35: 215–222 (1992).

Dominiguez et al., Immunogenetics 36:277–282 (1992).

Krausa et al., The Lancet 341: 121–122 (1993).

Fernandez–Viña et al., Human Immunology 33: 163–173 (1992).

*Primary Examiner*—W. Gary Jones
*Assistant Examiner*—Ethan Whisenant
*Attorney, Agent, or Firm*—Nixon & Vanderhye, PC

[57] ABSTRACT

The invention relates to a method for typing or subtyping one or more HLA-B alleles characterized by the sequence GCCA at position 30 to 33 of exon 2 (with said numbering being according to Zemmour and Parham, 1992), liable to be present in a sample, with said method comprising at least the following steps: (i) amplifying HLA-B alleles with at least one 5' end amplification primer selected from the following list: 5' -AGGTATTTCTACCCGCCA-3' (B25P) or sequence variants thereof, in combination with an appropriate 3' end primer being chosen from the same alleles as the above defined 5' end primers, with said 5' and 3' end primers being possibly labelled; and, (ii) hybridizing the amplified product, being labelled during or after amplification, at appropriate conditions with one or more suitable probes selected from region 15 to 261 of the HLA-B exon 2 region, with said numbering being according to Zemmour and Parham 1992, (iii) washing at appropriate washing conditions, (iv) detecting the hybrids formed; and, (v) inferring the allele present from the observed hybridization pattern.

4 Claims, 5 Drawing Sheets

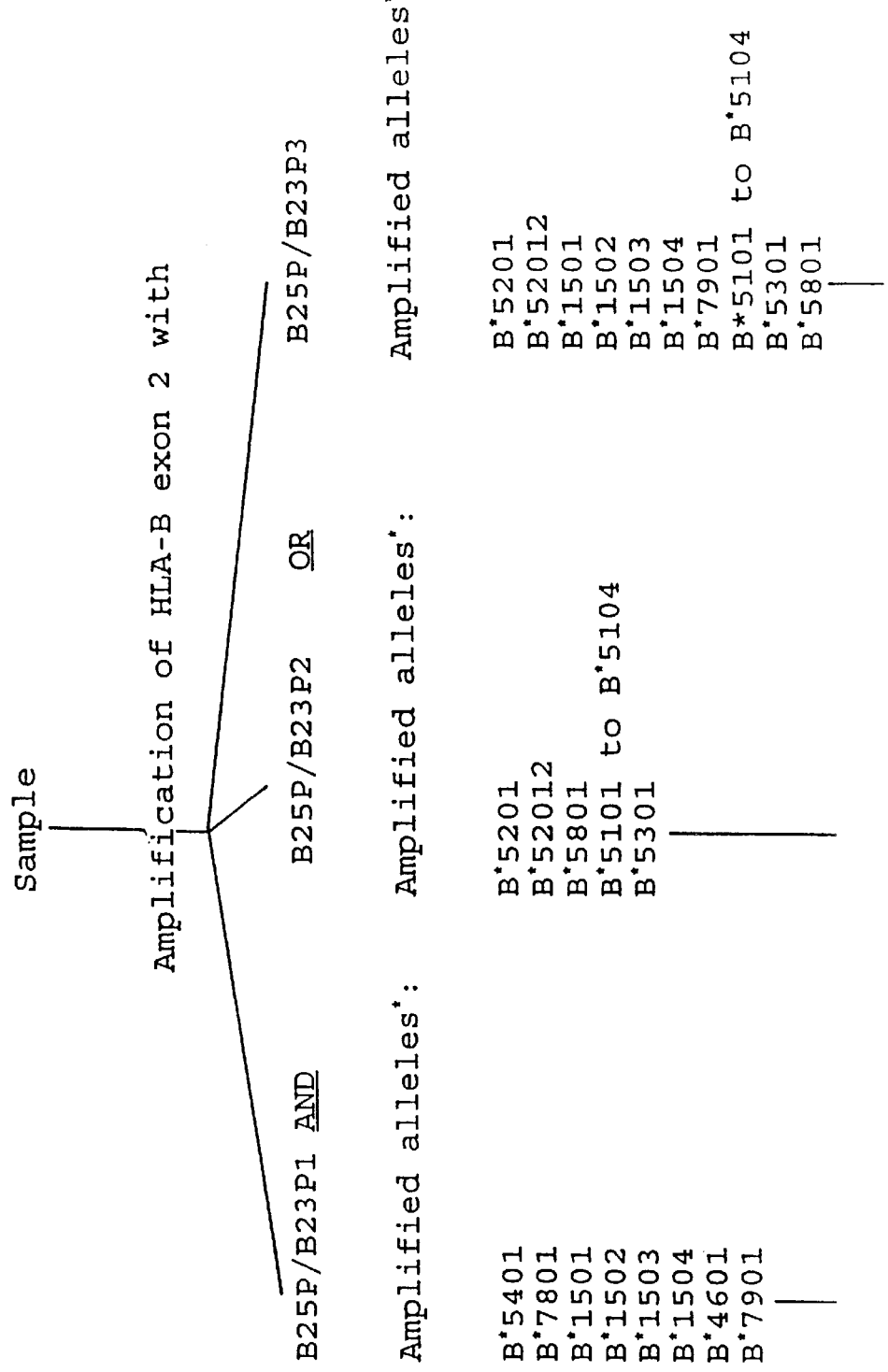

\* Only those which are the subject of the present invention are indicated

◀ Hybridizations with probe 17, 18, and 19 are not relevant since they are located at the distal end of the 3' end of the B23P3 primer § See Table 1.

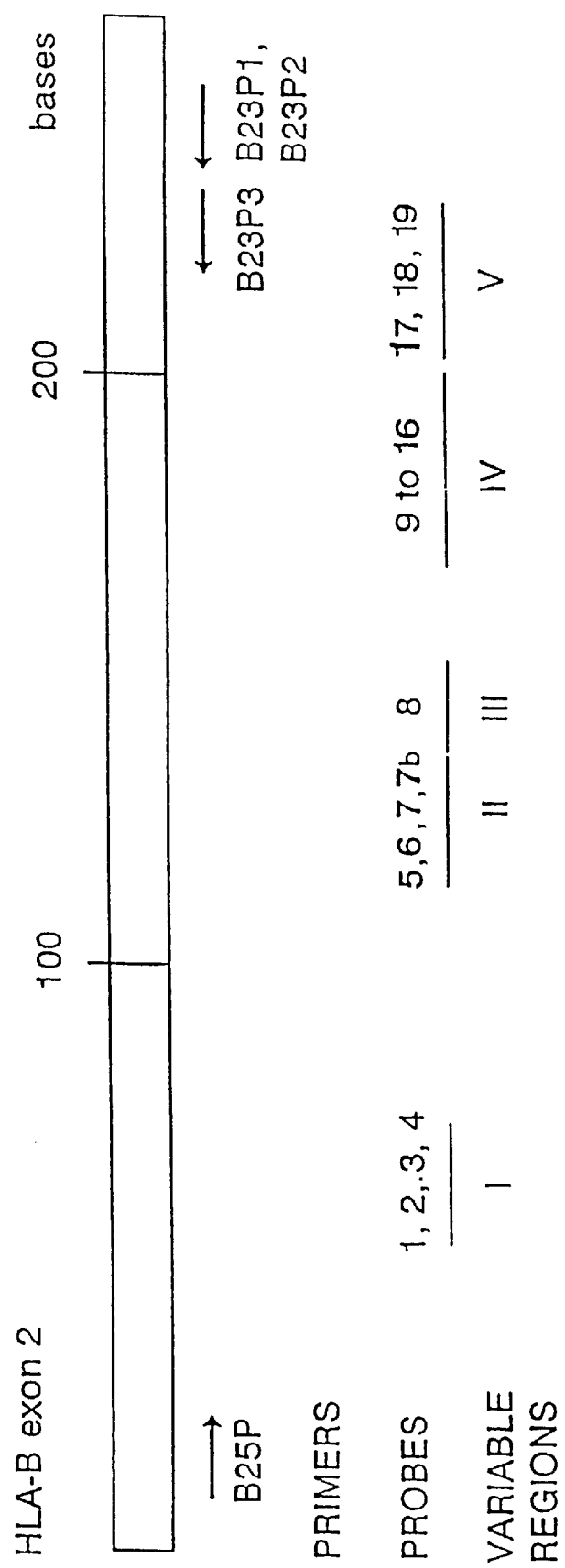

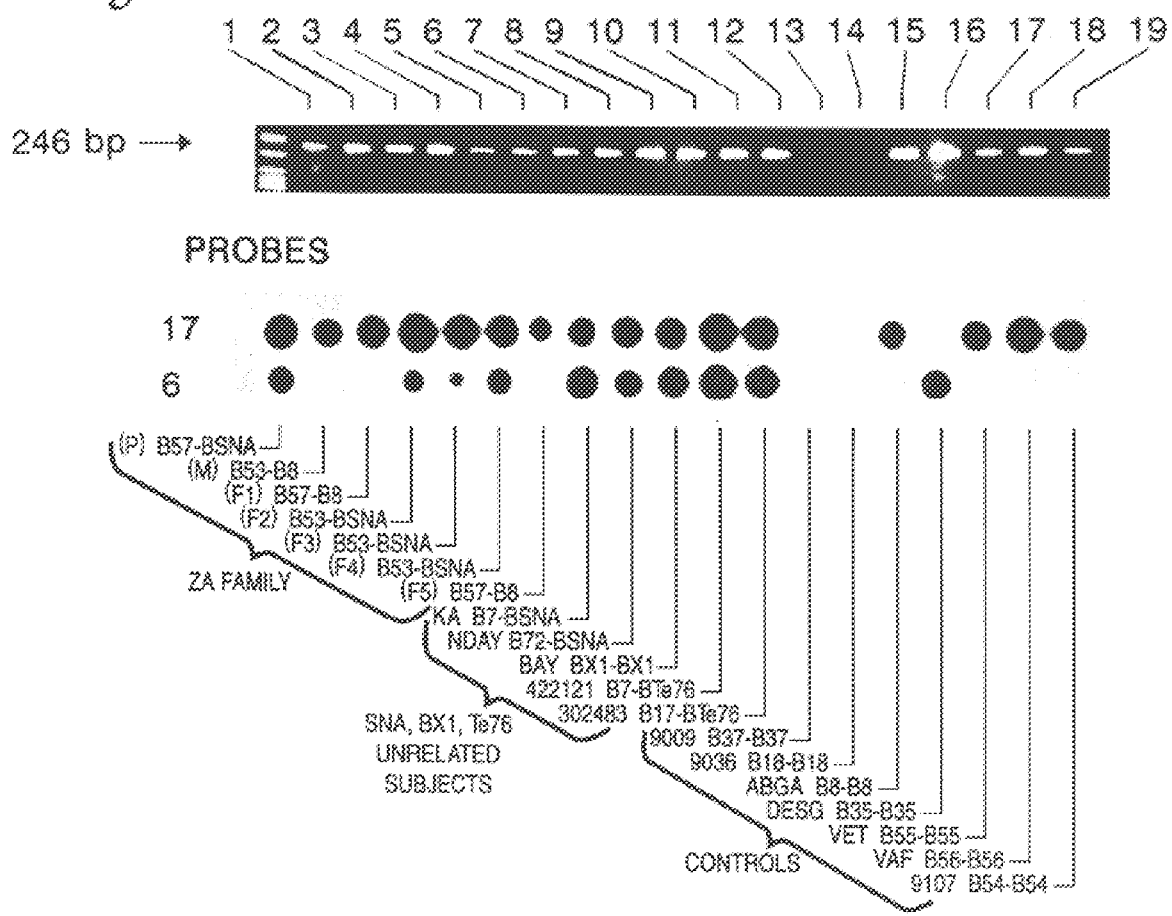

5,883,238

PROCESS FOR TYPING HLA-B USING SPECIFIC PRIMERS AND PROBES SETS

The invention relates to a process and reagents for DNA typing of HLA-B alleles.

The technical problem underlying the present invention is to provide a DNA typing method using specific primer and probe sets enabling the discrimination of HLA-B alleles, especially those which are difficult to discriminate by serological means.

The Human Leukocyte Antigen (HLA) system comprises a series of linked genes on the short arm of chromosome 6. Three classes of genes are defined: class I antigens (HLA A, B, C) composed of an $\alpha$ chain non covalently associated with $\beta 2$ microglobulin, encoded on chromosome 15; class II antigens (DP, DQ, DR) composed of an $\alpha$ and a $\beta$ chain; class III products which correspond to components of the complement system. Class I and class II antigens are polymorphic transmembrane glycoproteins and share a common immunologic role in antigen presentation. HLA class I restricted presentation of foreign antigens leads to cytotoxic T cell receptors in mature T lymphocytes. In addition, class I and class II antigens play a crucial role in transplantation immunology and in the susceptibility to autoimmune diseases.

Extensive polymorphisms exist at most loci. In view of the biological and medical importance of these antigens a highly sensitive and rapid technique for HLA typing is required. Different protocols have been used until now: serologic, cellular and DNA based restriction fragment polymorphism (RFLP) and recently also sequence specific oligonucleotide (SSO) hybridization methods. DNA typing by oligonucleotide hybridization provides the best direct definition of HLA polymorphisms next to complete sequence analysis. However, sequence analysis is expensive and time consuming and hence not the method of choice for routine applications.

Polymorphisms are of fundamental significance for the function of HLA antigens and will be mostly localized in exons coding for the functionally important extracellular domains.

For class I genes most of the polymorphisms are localized in the aminoterminal $\alpha 1$ and $\alpha 2$ domains. The $\alpha 3$ domain is a highly conserved immunoglobin-like domain. A total of 40 HLA A, 64 HLA B, and 24 HLA C alleles have been identified (Zemmour and Parham, Tissue Antigens, 40: 221–228,1992). Diversity between different alleles occurs in specific regions of the $\alpha 1$ and $\alpha 2$ domain. A patchwork pattern with short stretches of homology between different alleles occurs. Genetic mechanisms such as homologous recombination and exon shuffling have lead to locus specific allelic diversity (Parham et al. PNAS (USA) 85:4005–4009, 1988).

Different typing methods have been developed to discriminate between the different alleles of the very polymorphic class I and class II loci. An overview of these different typing methods is given below:

Serology: In a microtoxicity test antisera to different HLA class I or class II antigens are incubated with lysed purified lymphocytes. Lysed cells will be stained with eosin or other dyes while not-lysed cells will remain unstained. This method is used for class I A, B, C alleles and class II DR and DQ alleles. DP alleles cannot be typed due to too low level of expression and a limited availability of antisera. The reaction for class II alleles is performed on purified B lymphocytes. A limited determination of supertypic groups of alleles is possible without further subtyping. Three alleles of the HLA C locus remain serologically undefined. Since epitopes on the HLA molecule are detected, discrimination between the $\alpha$ and the $\beta$ chains is impossible and the $\alpha\beta$ hetrodimer is identified. Allosera against class II molecules are often anti-class I contaminated and need to be absorbed before use. Crossreactions between alleles on the same or on a different locus occur, which makes analysis of the result difficult. Even if monoclonal antibodies are used the problem of crossreactions is not solved. Although this is a very rapid method (3 hrs for complete typing), incomplete and erroneous results are the main problems.

Cellular methods: a mixed lymphocyte reaction (MLR) has been developed based on the proliferative response of T-cell cultures to stimulation by irradiated homozygous typing cells. Proliferation is measured by incorporation of $H^3$-Thymidine. This method is used for HLA class II typing of DR and DQ alleles. DP typing is also impossible because of the low level of its membrane expression. These analyses define the DW specificities that further subdivide the serological specificities. HLA DW specificities are determined by DR and DQ antigens but are almost always associated with a particular allele on the DR and DQ locus. A secondary MLR can be performed for HLA DP typing. This analysis is based on in vitro secondary or memory responses. When lymphocytes have responded to irradiated stimular cells, after 10 days of culture they revert from blast cells expansion to the production of small lymphocytes. These cells have the capacity to give a stronger and accelerated response in culture to irradiated stimulator cells which have to be typed and which share the antigen with the first stimulator cells that gave the initial positive reaction (Festenstein and Ollier, 1987). Although very complete and correct, this analysis is very time consuming and difficult to perform.

Different DNA typing methods were developed that have the advantage not to be linked to surface expression of the antigens. An overview of these DNA typing methods is given:

Restriction fragment length polymorphism (RFLP) methods: High molecular weight DNA is digested with several restriction enzymes, separated according to size by gel electrophoresis, blotted to filters and hybridised to HLA DQA, DQB, DPB or DRB cDNA probes. A distinct pattern of bands for the different alleles is obtained. Sequence analysis was used to find the different restriction site polymorphisms and to determine the different enzymes to be used. This method however has some disadvantages: large amounts of high-molecular weight DNA are needed, not many alleles can be distinguished, use of several restriction enzymes, detection of phenotypically irrelevant specific amino acid difference.

Polymerase Chain Reaction (PCR) methods: since the sequences of all class II alleles are known, locus-specific primers can be designed to amplify the polymorphic regions. After amplification, large amounts of specific sequences are analyzed by RFLP analysis or by SSO hybridization. The PCR product can be digested by different restriction enzymes and the fragments separated on gel by electrophoresis. An alternative is the hybridization method. Sequence-specific oligonucleotides (SSO's) are designed. Hybridization can be performed in a conventional dot blot procedure. PCR products are covalently bound to a membrane and hybridised to $^{32}P$ labelled SSOs. Other labelling methods are possible. Detection of positive signals is done by autoradiography. Since all. SSOs may differ in length and GC content different hybridisation temperatures are maybe needed for the different SSOs in the conventional dot-blot approach.

The conventional serological and cytological typing techniques for HLA class I antigens are well-established. However, erroneous results may occur due to the specificity of the antisera, the presence of auto-antibodies or medication. For HLA-B, typing problems are predominantly experienced with the following types:

| Serological Designation | Corresponding allele |
|---|---|
| B54 (22) | B*5401 |
| B52 (5) | B*5201/B*52012 |
| B78 | B*7801 |
| B62 (15) | B*1501/B*1504 |
| B75 (15) | B*1502 |
| B72 (70) | B*1503 |
| B71 (70) | not yet known |
| B46 | B*4601 |
| B79 | B*7901 |
| B58 (17) | B*5801 |
| B53 | B*5301 |
| B5102 (B5/B35) | B*5102 |
| B5103 (BTA) | B*5103 |

A DNA based typing system will greatly improve and accelerate identification of these difficult HLA-B types. As a consequence, this will have a beneficial impact on the success-rate of organ and bone-marrow transplantations and the total costs involved. There is ample evidence that a high correlation exists between the success-rate of transplantation and the HLA-B compatibility of the donor and the recipient.

In addition a more accurate HLA-B typing will also considerably improve or facilitate disease susceptibility studies and forensic investigations.

It should be noted that, in general, DNA typing methods should be preferred over serological typing provided that an easy, rapid and reliable DNA typing method is available. This is due to the fact that some differences at the subtype level (which are usually detectable by DNA methods) might go undetected by current serological typing methods, although these differences might provoke allograft rejection (Fleischhauer et al., New Eng. J. Med. 323: 1818–1822, 1990).

In contrast with successful application of molecular biology for the definition of HLA class II genes, development of class I molecular typing remains difficult. This is due to marked polymorphism, high complexity of nucleotides substitutions and presence of numerous non classical class I genes and pseudogenes existing in this region. Class I antigens are characterised by cross-reactivity among different alleles mostly within HLA-A and -B antigens defining serological cross-reactivity groups (CREGs). The HLA-A and B alleles are divided into respectively five and ten classical CREG families. Up to now, all known HLA-A specificities have been sequenced resulting in the definition of sequence homology explaining these cross-reactions and the recent capacity to use the polymerase chain reaction (PCR) using sequence specific primers (SSP). In contrast, the HLA-B alleles are characterized by a greater polymorphism and by a higher level of cross-reactivity. In addition, a substantial proportion of the B alleles have not yet been sequenced. Correlation between cross-reactivity and DNA sequences present some discrepancies.

The number of publications dealing with PCR and DNA probe typing of class I alleles are limited as compared to those for class II. Except for the paper of Yoshida et al. (1992, vide infra), the alleles which are the subject of the present invention are not covered in those studies. Summers et al. (Hum. Immunol. 32: 176–182, 1991) described the use of PCR of class I alleles for sequencing purposes. The combination of PCR and classical dot hybridizations with oligonucleotide probes for the discrimination of B44 alleles (B*4401, B*4402) was described by Fleischhauer et al. (N. Eng. J. Med. 323: 1818–1822, 1990). Two research groups reported on the DNA typing and subtyping of HLA-B27 alleles (Hill et al., The Lancet, 337: 640–642, 1991; Dominguez et al., Immunogenetics 36: 277–282, 1992). Hernandez-Viña et al. (Hum. Immunol. 33: 163–173, 1992) described oligonucleotide typing subsequent to PCR amplification for HLA-A2 and HLA-A28 alleles; and a more general typing approach for HLA-A alleles using the amplification refractory amplification system was recently described by Krausa et al. (The Lancet, 341: 121–122, 1993).

Yoshida et al. (Hum. Immunol. 34: 257–266, 1992) also combined PCR with a classical dot blot approach and/or single strand confirmation polymorphism analysis. They designed PCR-primer and probe combinations for typing of 26 HLA-B specificities. Their typing approach is primarily based on the use of differential amplification with primers discriminating between the Bw4 and Bw6 supratypes and the use of a HLA-B specific 5'-sided primer. With the primer sets and probes described, these authors did not discriminate the following alleles: B*5401, B*7801 and B*7901, which are also difficult to type by conventional methods. Neither can they discriminate between B*5201 and B*52012 nor between B53 and B51 alleles since sequence differences between these alleles are located outside the region amplified with their primers.

The present invention thus aims at providing a method for DNA typing or subtyping one or more HLA-B alleles by a hybridization approach.

More particularly the present invention aims at a method for DNA typing and/or subtyping of those HLA-B alleles of which the corresponding serological-typing procedure poses problems or is impossible. The most predominant alleles for which the serological typing procedure poses problems are the following:

| Serological Designation | Corresponding allele |
|---|---|
| B54 (22) | B*5401 |
| B52 (5) | B*5201/B*52012 |
| B78 | B*7801 |
| B62 (15) | B*1501/B*1504 |
| B75 (15) | B*1502 |
| B72 (70) | B*1503 |
| B71 (70) | not yet known |
| B46 | B*4601 |
| B79 | B*7901 |
| B58 (17) | B*5801 |
| B53 | B*5301 |
| B5102 (B5/B35) | B*5102 |
| B5103 (BTA) | B*5103 |

According to another embodiment, the present invention aims at providing sequence specific oligonucleotides which allow the DNA typing of HLA-B alleles for which the serological typing procedure poses problems such as selected from the above-presented list.

According to yet another embodiment, the present invention aims at providing sequence specific primers which allow the DNA typing of HLA-B alleles for which the serological typing procedure poses problems such as selected from the above-presented list.

The present invention also aims at providing compositions or solid supports comprising at least one of the above-mentioned sequence specific oligonucleotides and/or specific primers.

More particularly, the method of the invention aims at amplifying exon 2 of a specific subset of HLA-B alleles, corresponding to the alleles for which the serological typing procedure causes problems, by means of specific primers (SPs) and subsequently hybridizing the amplified products to an appropriate set of sequence specific oligonucleotides (SSOs) covering the amplified region of the HLA-B exon 2.

The present invention also aims at providing kits for DNA typing of HLA-B alleles for which the serological typing procedure poses problems such as selected from the above-presented list.

The present invention meets the above-mentioned aims by providing novel processes and reagents. More particularly, the present invention meets the above-mentioned needs by providing a specific set of specific primers (SPs) and sequence specific oligonucleotides (SSOs), and kits for practicicing said methods, that toghether provide a rapid, simple and precise system for typing the alleles at the HLA-B genes.

The novel process and reagents according to the invention may in turn lead to the discovery of previously unknown HLA-B alleles, which can also be typed and identified by the present method. Also some other types (not listed in the table above) may cause typing difficulties by serology such as B76, B77, B61, B67 and B59. Although the nucleic acid sequences are not yet known, it is sometimes possible to predict whether or not these specificities can be typed using the approach of this invention. This will be exemplified further herein for B71.

The expression "typing or subtyping" is to be understood as determining and/or discriminating the type or subtype present in a biological sample. By type or subtype is understood all variants which may be discriminated by said typing method. In the case of discriminating the type of one allele, the typing method determines the presence of said specific allele.

The officially recognized serological types (also called HLA specificities) and their corresponding alleles (if the sequence is known) are compiled in an annually updated reference list (Bodner et al., Tissue Antigens, 39:161–173, 1992).

The method of the invention is based on an amplification of exon 2 of a subset of HLA-B alleles possibly present in the sample with particular sets of amplification primers (also referred to as SPs). Subsequently the amplified products are hybridized to an appropiate set of DNA probes (also referred to as SSOs) after which the hybrids formed are detected and the HLA-B type deduced from the hybridization pattern generated. In this approach, particularly aiming at the identification of types which are difficult to distinguish or not distinguishable at all by serological techniques, it is particularly advantageous that the 5'end amplification-primer specifically targets the region 30 to 33 in exon 2 of the HLA B alleles (according to the numbering given by Zemmour and Parham, 1992). According to the sequence data given by these authors, all known alleles which can be determined according to the present invention have the following sequence at position 30 to 33 in exon 2: 5'-GCCA-3'. Hence, an amplification-primer ending on this sequence will amplify all alleles wanted, and will simultaneously exclude the amplification of exon 2 of many other HLA B-alleles (which are characterized by the corresponding sequence 5'-TCCG-3' at position 30 to 33 of exon 2) hereby considerably simplifying the DNA typing approach. HLA-B exon 2 alleles of which the DNA-sequence is known (Zemmour and Parham, 1992) and which are characterized by the sequence 5'-GCCA-3' at position 30 to 33 are listed in Table 1.

The invention thus relates to a method for typing or subtyping one or more HLA-B alleles in a sample characterized by the sequence 5'-GCCA-3' at position 30 to 33 of exon 2 of said HLA-B allele (with said numbering being according to Zemmour and Parham, 1992), and more particularly a method for discriminating HLA-B types which are serologically difficult to discriminate such as for instance B54(22), B52(5), B7801, B62(15), B75(15), B71(70), B72(70), B46, B79, B53, B5102, B5103 and B58(17), with said method comprising at least the following steps:

(i) possibly extracting sample nucleic acid, (ii) amplifying the nucleic acid of HLA-B alleles characterized by the sequence 5'-GCCA-3' at position 30 to 33 of exon 2 of said HLA-B allele with at least one 5' end amplification primer selected from the following list:

| 5'-AGGTATTTCTACACCGCCA-3' | (B25P, SEQ ID NO 1) | or sequence variants thereof, such as:

| 5'-AGGTATTTCCACACCGCCA-3' | (SEQ ID NO 2) |
| 5'-AGGTATTTCGACACCGCCA-3' | (SEQ ID NO 3) | or other sequence variants, with said sequence variants containing deletions, and/or insertions, and/or substitutions of one or more nucleotides provided that the 3' end GCCA sequence is retained and that these sequence variants can be caused to specifically amplify the same HLA-B alleles as the B25P primer or variants thereof as designated above, in combination with an appropriate 3' end primer being chosen from the same alleles as the above defined 5' end primers, with said 5' and 3' end primers being possibly labeled; and, (iii) hybridizing the amplified product, being possibly labeled during or after amplification, at appropriate conditions with one or more suitable probes selected from region 15 to 261 of the HLA-B exon 2 region, with said numbering being according to Zemmour and Parham, 1992, (iv) washing at appropriate washing conditions, (v) detecting the hybrids formed; and, (vi) inferring the allele present from the observed hybridization pattern.

In order to perform the process of the invention as illustrated above, it may be necessary to perform an extraction of sample nucleic acid according to any of the techniques known in the art. In case of extraction of RNA, generation of cDNA is necessary; otherwise cDNA or genomic DNA is extracted.

The term "primer" refers to a single stranded DNA oligonucleotide sequence or specific primer (SPs) capable of acting as a point of initiation for synthesis of a primer extension product which is complementary to the nucleic acid strand to be copied. The length and the sequence of the primer must be such that they allow to prime the synthesis of extension products. Preferably the primer is about 5–50 nucleotides, more preferably from about 10 to 21 nucleotides. Specific length and sequence of the primer will depend on the complexity of the required DNA or RNA targets, as well as on the conditions of primer use such as temperature and ionic strength.

The fact that amplification-primers do not have to match exactly with the corresponding template sequence to warrant proper amplification, providing that an exact match at the last three nucleotides at the 3' end of the primer is maintained, is amply documented in the literature (Kwok et al., Nucleic Acids Research 18:999–1005, 1990; Sommer and Tautz, Nucleic Acids Research 17, 6749, 1989).

The term "probe" refers to single stranded sequence-specific oligonucleotides. (SSO's) which have a sequence which is exactly complementary to the target sequence of the allele to be detected.

Preferably, these probes are about 5 to 50 nucleotides long, more preferably from about 10 to 18 nucleotides.

The expressions "appropriate" hybridization and washing conditions refers to the fact that in most cases said probes are to hybridize only to exactly complementary sequences. Such conditions are examplified in the Examples section. For instance for probe 17 preferred hybridization and wash temperatures are respectively 54° C. and 58° C. if 3M TMAC is used as hybridization and wash solution. In general, the hybridization conditions are to be stringent as known in the art (f.i. Maniatis et al., Molecular Cloning: A Laboratory Manual, New York, Cold Spring Harbor Laboratory, 1982).

However, according to the hybridization solution (SSC, SSPE, etc.), these probes should be hybridized at their appropriate temperature in order to attain sufficient specificity (in most cases differences at the level of one point mutation should be discriminated). The above-mentioned 5' end primers are referred as B25P primers.

The term "sample" refers to any source of biological material, for instance blood stains, hair, epithelial cells or peripheral blood cells. Typical samples may include peripheral blood mononuclear cells (PBMNC's), lymphoblastoid cell lines (LCL's), hair cells or the like. The preferred isolated nucleic acid will be genomic DNA. However, cytoplasmic, cellular and poly(A)+RNA may also be used.

The expression "inferring the allele present from the observed hybridization pattern" refers to the central feature of the HLA-B typing method of the present invention which involves the identification (also referred to as determination or discrimination) of the HLA-B alleles present in the sample by analyzing the pattern of binding of a panel of oligonucleotide probes. Although single probes may also provide useful information, the variation of the HLA-B alleles is dispersed in nature, so rarely is any one probe able to identify uniquely a specific variant. Rather, as shown in the Examples, the identity of an allele is inferred from the pattern of binding of a panel of oligonucleotide probes, which are specific for different segments of the different HLA-B alleles. Depending on the choice of these oligonucleotide probes, each known allele will correspond to a specific hybridization pattern upon use of a specific combination of probes. Each allele will also be able to be discriminated from any other allele amplified with the same primers depending on the choice of the oligonucleotide probes. Comparison of the generated pattern of positively hybridizing probes for a sample containing one or more unkown HLA-B allele to a scheme of expected hybridization patterns as for instance shown in Table 1, allows one to clearly infer the HLA-B alleles present in said sample.

Since the targeted alleles differ somewhat in sequence at the 3'-end of exon 2 (Zemmour and Parham, 1992), different 3' end primers should be combined with a 5' end primer (B25P or variants thereof) to accomplish specific amplification of all alleles of interest.

The present invention thus relates to a method as defined above, characterized further in that at least one of the following 3' end amplification primers (B23) is used:

5'-TCTGGTTGTAGTAGCCGCGCA-3' (B23P1, SEQ ID NO 4), or sequence variants thereof, such as:

5'-TCTGGTTGTAGTAGCGGAGCG-3' (B23P2, SEQ ID NO 5),

5'-TCCGCAGGTTCTCTCGGTA-3' (B23P3, SEQ ID NO 6), or other sequence variants, with said sequence variants containing deletions, and/or insertions, and/or substitutions of one or more nucleotides provided that these sequence variants can be caused to specifically amplify the same HLA-B alleles as the B23P1 primer or variants B23P2 or B23P3 as designated above, with said primers being possibly provided with a detectable label, such as biotin.

As indicated, these primers will be further referred to as B23P1, B23P2, and B23P3, respectively. Primers B23P1 and B23P2 target the region 241 to 261 in HLA B exon 2; primer B23P3 targets the region 219 to 237 (numbering according to Zemmour and Parham, 1992). The alleles of which the DNA-sequence corresponds completely with the 3'end of the primers mentioned above, are identified in Table 1.

From these data, it can be concluded that in order to achieve amplification of all HLA-B alleles of interest, the amplification with primer set

B25P/B23P1 should at least be combined with one of the following sets:

B25P/B23P2 or,

B25P/B23P3.

From the data given in Table 1, it can also be concluded that some alleles are amplified exclusively with one primer set and not with one of the other combinations set forward. E.g. among other alleles, B*4601 or B*7801 are only amplified with primer set B25P/B23P1. Whereas for instance alleles B*1503 or B*5801 are amplified with the primersets B25P/B23P1 and B25P/B23P3, and B25P/B23P2 and B25P/B23P3 respectively. It should also be mentioned that from the available sequence data (Zemmour and Parham, 1992) other 3' end amplification primers may be selected with which amplification of a particular part of HLA-B exon 2 alleles may be achieved if combined with 5'-end primer B25P or variants thereof.

In one embodiment of the invention, amplification with the two primer sets of choice is performed in different reaction tubes and the amplified products are hybridized separately as indicated in the typing scheme in FIG. 1.

In another embodiment of the invention, amplification with the two primer sets of choice is performed in different reaction tubes and the amplified products are mixed after amplification and hybridized together.

In a preferred embodiment of the invention, the different primers involved (either B25P, B23P1 and B23P2 or B25P, B23P1 and B23P3) are mixed and amplification is performed in a single reaction tube after which the amplified products are hybridized together.

The amplification method used can be either PCR (Saiki et al., Science 239:487–491, 1988), nucleic acid sequence-based amplification (NASBA, Guateli et al., PNAS (USA) ;87:1874–1878, 1990; Compton, Nature;350:91–92, 1991), transcription-based amplification system TAS, Kwoh et al., Proc. Natl. Acad. Sci. (USA) 86:1173–1177, 1989), strand displacement amplification (SDA, Duck et al., Biotechniques 9:142–147, 1990; Walker et al. Proc. Natl. Acad. Sci. (USA) 89:392–396, 1992), amplification by means of Qβ replicase (Lizardi et al., Bio/Technology 6:1197–1202, 1988; Lomeli et al., Clin. Chem. 35:1826–1831, 1989) or any other suitable method liable to amplify nucleic acid molecules using primer extension. During amplification, the amplified products can be conveniently labeled either using labeled primers or by incorporating labeled nucleotides. Labels may be isotopic ($^{32}$P, $^{35}$S, etc.) or non-isotopic (biotin, digoxigenin, etc.).

In order to distinguish the amplified alleles from each other, the amplification products are hybridized to a set of sequence-specific DNA probes (also referred to as SSOs) targetting HLA-B exon 2 regions located in between the amplification primer regions chosen. Different hybridization formats can be used such as the conventional dot-blot format, sandwich hybridization or reverse hybridization (such as the reversed dot blot format). A particular set of DNA probes was selected which enables to distinguish the alleles of interest from each other and from other alleles described, whether or not these alleles are present in the homozygous or heterozygous state.

For this purpose, 20 basic DNA probe sequences were identified which are designed to be functional in TMAC (tetramethylamonium chloride) hybridization and wash conditions as illustrated in the Examples section. Most of these probes target the most variable regions of HLA-B exon 2 and can be caused to hybridize to more than one HLA-B allele. Some probes were selected because they are allele-specific; these probes are probe 8 (SEQ ID NO 14), 12 (SEQ ID NO 18), and 16 (SEQ ID NO 22), which exclusively hybridize to B*5401, B*4601, and B*7901 respectively. The regions targeted by the different probes are schematically represented in FIG. 2. In Table 2, the sequences of the probes are given. An interpretation is given in Table 1. Further on, the same 20 basic probes or variants thereof were tested in hybridization and wash conditions specific for SSPE as reviewed in Example 5 and Table 2 bis. As can be seen in Table 2 bis, 9 of the originally TMAC-tested probes and some of the new variant probes are particularly preferred above others under the specific SSPE buffer conditions used.

The present invention thus relates to a method as defined above, wherein one or more hybridization probes are selected from Table 2 (SEQ ID NO 7 to 26), or sequence variants thereof, with said sequence variants containing deletions and/or insertions of one or more nucleotides, mainly at their extremities (either 3' or 5'), or substitutions of some non-essential nucleotides (i.e. nucleotides not essential to discriminate between alleles) by others (including modified nucleotides such as inosine), or with said variants consisting of the complement of any of the above-mentioned oligonucleotide probes, or with said variants consisting of ribonucleotides instead of deoxyribonucleotides, all provided that said variant probes can be caused to hybridize with the same specificity as the oligonucleotide probes from which they are derived.

The latter implies that variants contemplated within this aspect of the present invention can be defined as probes hybridizing with the same specificity as the probe they are derived from under different, but stringent, hybridization and wash conditions (different solutions, different concentrations of buffer, different concentrations of probe, different temperatures). Such variants are f.i. contained within the sequences given in SEQ ID NO 27 to 52 (Table 2 bis).

According to the hybridization solution (SSC, SSPE, TMAC, etc.), these probes should be stringently hybridized at their appropriate temperature in order to attain sufficient specificity (in most cases differences at the level of one point mutation should be discriminated). However, by slightly modifying the DNA probes listed in Table 2, either by adding or deleting one or a few nucleotides at their extremities (either 3' or 5'), or substituting some non-essential nucleotides (i.e. nucleotides not essential to discriminate between alleles) by others (including modified nucleotides such as inosine) these probes or variants thereof can be caused to hybridize specifically at the same hybridization conditions (i.e. the same temperature and the same hybridization solution). Also changing the amount (concentration) of probe used relevant to each other may be beneficial to obtain more specific hybridization results. It should be noted in this context, that in contradiction to SSPE based buffer solutions, probes of the same length, regardless of their GC content, will hybridize specifically at approximately the same temperature in TMAC solutions (Jacobs et al., Nucleic Acids Research 16:4637–4650, 1988).

Preferred basic and variant probes using different hybridization and wash buffer conditions are illustrated in the Examples section of the present invention. Some of these preferred probes are included in SEQ ID NO 7 to 52.

Among the alleles which are the subject of this invention, B*1501 and B*1504 cannot be discriminated from each other since these sequences are exactly the same in the second exon. Differences between both alleles are found in the 5' end of exon 3 (Zemmour and Parham, 1992). For the same reason B*5101 to B*5104 cannot be distinguished. Also for these alleles discrimination can be achieved in exon 3 (Zemmour and Parham, 1992). Thus a more complete typing system will include a primer and probe combination to discriminate between types in exon 3.

The above-mentioned DNA typing methods in which primer pair B25P/B23P2 is used and hybridization is observed with SSO's 7 (SEQ ID NO 13) and 9 (SEQ ID NO 15) are preferably carried out additionally and separately with primer pair B25P and the B23P1 and/or B23P3 primers. For the latter application, a primer with the following sequence:

5'-GACGACACG/CCT/AGTTCGTGA-3
B25PX1 (SEQ ID NO 53)

can be used as alternative for the B25P primer.

As detailed in the Examples section, this additional amplification step rules out the possibility that co-amplification of the HLA-AR pseudogene (when primer B23P2 is used) occurs, and thus allows for a more accurate HLA-B typing procedure.

Suitable assay methods for purposes of the present invention to detect hybrids formed between the oligonucleotide probes and the nucleic acid sequences in a sample may comprise any of the assay formats kown in the art. For example, the detection can be accomplished using a dot blot format, the unlabelled amplified sample being bound to a membrane, the membrane being incorporated with at least one labelled probe under suitable hybridization and wash conditions, and the presence of bound probe being monitored. Probes can be labelled with radioisotopes or with labels allowing chromogenic or chemilumeniscent detection such as horse-radish peroxidase coupled probes.

An alternative is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of typing of HLA-B alleles contained in a biological sample comprises the steps of contacting amplified copies derived from the genetic material, with a solid support on which probes as defined above, have been previously immobilized.

The term "solid support" can refer to any substrate to which an oligonucleotide probe can be coupled, provided that it retains its hybridization characteristics and provided that the background level of hybridization remains low. Usually the solid substrate will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic groups, $NH_2$ groups, SH groups, carboxylic groups, or coupling with biotin or haptens.

According to another advantageous embodiment, the process of typing of HLA-B alleles contained in a biological sample comprises the steps of contacting amplified copies derived from the genetic material, with oligonucleotide probes which have been immobilized as parallel lines on a solid support.

According to this preferred embodiment of the invention, one or more of the above defined probes are used for immobilization and incorporation into a reverse phase hybridization assay, preferably for immobilization as parallel lines onto a solid support such as a membrane strip, for typing of HLA-B alleles according to a method as defined above. According to this advantageous method, the probes are immobilized in a Line Probe Assay (LiPA) format. This is a reverse hybridization format (Saiki et al., PNAS (USA); 86:6230–6234, 1989) using membrane strips on which 20 or more oligonucleotide-probes (including negative or positive control oligonucleotides) are conveniently applied as parallel lines. The LiPA strips are prepared as described by Stuyver et al. (J. Gen. Virol. 74: 1093–1102, 1993).

The invention thus also relates to a solid support, preferably a membrane strip, carrying on its surface, one or more probes as defined above, coupled to the support in the form of parallel lines.

The LiPA is a very rapid and user-friendly hybridization test. Results can be read 4 h. after the start of the amplification. After amplifiaction during which usually a non-isotopic label is incorporated in the amplified product, and alkaline denaturation, the amplified product is contacted with the probes on the membrane and the hybridization is carried out for about 1 to 1.5 h. After a brief wash (10 to 30 min.) the detection procedure is started. All these steps are carried out in the same hybridization recipients, hereby minimalizing hands-on time. From the hybridization pattern generated, the HLA-B allele(s) present can be deduced either visually but preferably using dedicated software. The LiPA format is completely compatible with commercially available scanning devices, thus rendering automatic interpretation of the results very reliable. All those advantageous make the LiPA format liable for the use of HLA typing in a routine setting. The LiPA format should be particularly advantageous for typing those alleles which are difficult to type by routine serological means.

The present invention also relates to a method for detecting and identifying novel HLA-B alleles, different from the known HLA-B alleles, comprising the steps of:
 determining which HLA-B allele(s) the is(are) present in a biological sample, according to the process as defined above,
 in the case of observing a sample which does not generate a hybridization pattern compatible with those defined in Table 2, sequencing the portion of the HLA-B exon 2 sequence corresponding to the aberrantly hybridizing probe of the new HLA-B allele to be determined.

The probe set of the present invention does not only allow one to discriminate the alleles of which the sequences are known but also alleles with as yet unknown sequences can be detected as is exemplified in Example 3. In this example it is shown that B71 can be distinguished from B72 (B*1503) using probe 13. This is particularly advantageous since discrimination of B71 and B72 on serological basis is problematic.

The invention thus relates to a method for discriminating between B72 (B*1503) and non-B72 HLA-B alleles of the B70 group (B70, B71, i.e. alleles different from B*1503), using the method as defined above, with said non-B72 HLA alleles being characterized by the fact that they do not form a hybrid with at least one of the following probes which hybridize to the B*1503 allele (f.i. probe 13 (SEQ ID NO 19), probe 7 (SEQ ID NO 13), probe 10 (SEQ ID NO 16), probe 18 (SEQ ID NO 24), and probe 19 (SEQ ID NO 25)).

Once the sequence of these new alleles become available, new probes can be deduced which allow for a specific detection of these new alleles. The addition of these probes to the set of 20 basic probes listed in Table 1 will thus improve the level of discrimination and the relevance of this typing procedure.

The present invention thus also relates to a novel HLA-B allele corresponding to an as yet, at the nucleic acid sequence level unidetermined B70 HLA-B type, determined according to the above defined method, with said allele being characterized by the fact that it forms a hybrid with probe 2 (SEQ ID NO 8, see Table 2), whilst not forming a hybrid with probe 13 (SEQ ID NO 19, see Table 2), and with said allele being different from the HLA-B B70 allele B*1503 in at least one nucleotide position in the region spanning nucleotides 192 to 209, with said numbering being according to Zemmour and Parham, 1992.

The present invention also relates to a composition comprising at least one of the oligonucleotide amplification primers selected from the following list:

| | |
|---|---|
| 5'-AGGTATTTCTACACCGCCA-3' | (B25P, SEQ ID NO 1) | or sequence variants thereof, such as:

| | |
|---|---|
| 5'-AGGTATTTCCACACCGCCA-3' | (SEQ ID NO 2) |
| 5'-AGGTATTTCGACACCGCCA-3' | (SEQ ID NO 3) | or other sequence variants thereof, with said sequence variants containing deletions and/or insertions and/or substitutions of one or more nucleotides provided that the 3' end GCCA sequence is retained and that these sequence variants can be caused to specifically amplif the same HLA-B alleles as the B25P primer or variants thereof as designated above,

| | |
|---|---|
| 5'-TCTGGTTGTAGTAGCCGCGCA-3' | (B23P1, SEQ ID NO 4), | or other sequence variants thereof, such as:

| | |
|---|---|
| 5'-TCTGGTTGTAGTAGCGGAGCG-3' | (B23P2, SEQ ID NO 5), |
| 5'-TCCGCAGGTTCTCTCGGTA-3' | (B23P3, SEQ ID NO 6), | or sequence variants thereof, with said sequence variants containing deletions and/or insertions and/or substitutions of one or more nucleotides provided that sequence variants can be caused to specifically amplify the same HLA-B alleles as the B23P1 primer or variants B23P2 or B23P3 thereof as designated above, with said primers being possibly provided with a detectable label, such as biotin, and with set primers being possibly immobilized onto a solid support.

Preferably such compositions contain at least two or more amplification primers selected from said list. More preferably the amplification primer set B25P/B23P1 is combined with at least one of the following sets:

B25P/B23P2, or B25P/B23P3.

In addition to the above-mentioned components, said composition may also comprise at least one of the following primers:

5'-GACGACACG/CCT/AGTTCGTGA-3' B25PX(SEQ ID NO 53)

The present invention also relates to a composition comprising at least one oligonucleotide probe selected from the following list of probes:
SEQ ID NO 7, SEQ ID NO 8, SEQ ID NO 9, SEQ ID NO 10, SEQ ID NO 11, SEQ ID NO 12, SEQ ID NO 13, SEQ ID NO 14, SEQ ID NO 15, SEQ ID NO 16, SEQ ID NO 17, SEQ ID NO 18, SEQ ID NO 19, SEQ ID NO 20, SEQ ID NO 21, SEQ ID NO 22, SEQ ID NO 23, SEQ ID NO 24, SEQ ID NO 25, or SEQ ID NO 26, (as given in Tables 2), or sequence variants thereof, with said sequence variants containing deletions and/or insertions of one or more nucleotides, mainly at their extremities (either 3' or 5'), or substitutions of some non-essential nucleotides (i.e. nucleotides not essential to discriminate between alleles) by others (including modified nucleotides such as inosine), or with said sequence variants consisting of the complement of any of the above-mentioned oligonucleotide probes, or with said sequence variants consisting of ribonucleotides instead of deoxyribonucleotides, all provided that said variant probes can be caused to hybridize with the same specificity as the oligonucleotide probes from which they are derived. Such variants may f.i. be chosen from the following list of probes:
SEQ ID NO 27, SEQ ID NO 28, SEQ ID NO 29, SEQ ID NO 30, SEQ ID NO 31, SEQ ID NO 32, SEQ ID NO 33, SEQ ID NO 34, SEQ ID NO 35, SEQ ID NO 36, SEQ ID NO 37, SEQ ID NO 38, SEQ ID NO 39, SEQ ID NO 40, SEQ ID NO 41, SEQ ID NO 42, SEQ ID NO 43, SEQ ID NO 44, SEQ ID NO 45, SEQ ID NO 46, SEQ ID NO 47, SEQ ID NO 48, SEQ ID NO 49, SEQ ID NO 50, SEQ ID NO 51, or SEQ ID NO 52 (as given in Table 2 bis).

Preferably such compositions contain at least two, three or more of these probes.

The present invention also relates to a kit for typing at least one HLA-B allele from a biological sample liable to contain it, comprising the following components:
when appropriate at least one amplification primer chosen among any of those defined above,
at least one probe, with said probe(s) being preferentially immobilized on a solid substrate, and more preferentially on one and the same membrane strip, and with said probe(s) being selected among any of those defined above,
a buffer or components necessary for producing the buffer enabling hybridization reaction between these probes and the amplified product to be carried out;
when appropriate, a means for detecting the hybrids resulting from the preceding hybridization.

The present invention relates also to a kit for typing of at least one HLA-B allele from a biological sample liable to contain it, more particularly of a sample liable to contain serologically difficult to discriminate HLA-B types, subsequent to amplification of the nucleotides encoding the HLA-B alleles present in said sample, using one or more primer set combination according to a method as defined above, comprising:
at least one probe, with said probe(s) being preferentially immobilized on a solid substrate, and more preferentially on one and the same membrane strip, with said probe(s) being selected among any of those defined above,
a buffer or components necessary for producing the buffer enabling hybridization reaction between these probes and the amplified product to be carried out;
means for detecting the hybrids resulting from the preceding hybridization,
possibly also including an automated scanning and interpretation device for interpretating the results and inferring the allel present from the observed hybridization pattern.

FIGURE AND TABLE LEGENDS

FIG. 1 and FIG. 1A: Schematic representation of the typing approach according to the present invention.

FIG. 2: Localization of the primers and probes of the present invention on an axis representing exon 2 of the HLA-B gene. The numbering is according to Zemmour and Parham, 1992.

FIG. 3: Amplification (top panel) and dot-blot hybridization (bottom panel) results obtained with 13 patient-samples and 7 controls. The material was amplified using primer set B25P/B23P1, dot-blotted, and hybridized with probes 6 (SEQ ID NO 12) and 17 (SEQ ID NO 23) as described in examples 1 and 2.

Figure 4:
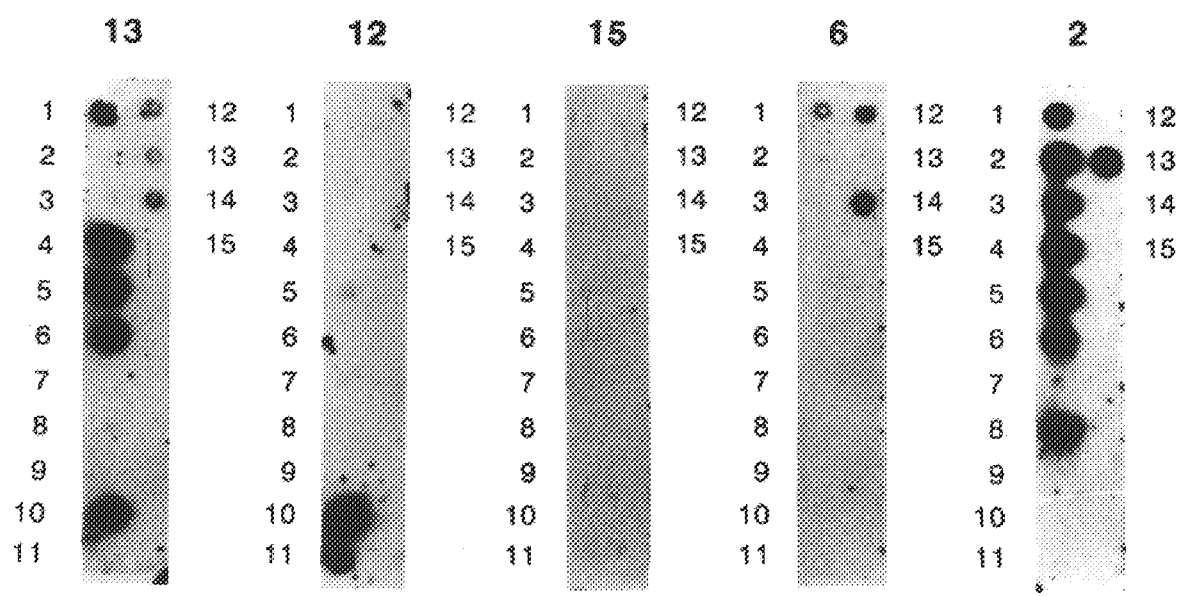

FIG. 4: Dot-blot hybridization results obtained for 15 samples (n* 1 to 15), among which samples harbouring B70 variant alleles and B46 alleles. The amplified material was applied to nylon membranes. Subsequently these membranes were hybridized with SSO-probes 13 (SEQ ID NO 19), 12 (SEQ ID NO 18), 15 (SEQ ID NO 21), 6 (SEQ ID NO 12), and 2 (SEQ ID NO 8) as indicated. The results are discussed in examples SSO 3 and 4 and summarized in Table 3.

Table 1: Amplified HLA-B alleles (exon 2) with the primer sets of the invention. Also the presence of the 3' end primer sequence in the alleles and the hybridization pattern with the set of the 19 SSO-probes is indicated.

Table 2: Panel of typing SSO-probes for HLA-B alleles.

Table 2 bis: Panel of typing SSO-probes for HLA-B alleles tested to be used in a reverse hybridization (Line Probe Assay, LIPA) format. All of these probes are derived from the basic set of 20 SSOs given in Table 2. The preferred probes are indicated as "+".

Table 3: Summary of the hybridization results obtained with 15 amplified samples hybridized with 5 SSO-probes as described in examples 3 and 4. See also FIG. 4.

Table 4: Hybridization results obtained with a LiPA strip onto which 20 oligonucleotide probes were immobilized. Positive hybridization signals after hybridization with material obtained respectively after amplification 1 and 2 (see Example 6) are indicated as "+".

ABBREVIATIONS

TMAC: Tetramethylamoniumchloride
SSO: Sequence-specific oligonucleotide
DIG 11-ddUTP: Digoxigenin-11-2',3'-dideoxy-uridine-5'-triphosphate
DIG: Digoxigenin
AMPPD: 3-(2'-spiroadamantane)4 methoxy-4-(3"-phosphoryloxy)-phenyl-1'2-dioxetane
AP: alkaline phosphatase

EXAMPLES

Example 1

Specific Amplification of Certain HLA-B Alleles with Primer Set B25P/B23P1

By way of example the amplification—specificity with one of the primer sets is illustrated. As indicated in FIG. 3, 12 samples and 7 controls were amplified with primer-set B25P/B23P1 (SEQ ID NO 1 and 4). Starting from cell-material, genomic DNA was prepared by standard protocols. Approximately 0.5 µg of genomic DNA was mixed with PCR buffer containing 12.5 pmoles of each primer; 200 mM of each dNTP (Pharmacia LKB Biotechnology, Uppsala, Sweden); 10 mM Tris HCl (pH 8.5); 50 mM KCl; 1 mM $MgCl_2$; 0.01% gelatine; 0.025% NP-40 and 1 Unit of Taq (Thermus aquaticus) DNA polymerase (Boerhinger, Mannheim GmbH, FRG) adjusted to a final volume of 50 µl with double distilled water. Samples were heated at 95° C. for 10 min and subjected to 35 cycles of PCR, each consisting of 94° C. for 1 min, 55° C. for 30 sec, 72° C. for 1 min with a 10 min 72° C. final extension in a DNA Thermal Cycler (Techne and Perkin-Elmer Cetus Corp., Norwalk, Conn.). The amplification products were characterized by a 1.5% agarose gel electrophoresis.

The results are shown in FIG. 3. In all samples in which amplifiable alleles were present a distinct band of about 246 basepairs, as predicted by the available sequence data, was observed after ethidiumbromide staining.

Samples 1, 4, 5, 6, 8, 9, 10, 11, and 12 harbour the B*7801 allele (indicated in FIG. 1 as BSNA, BX1 or BTe76). In sample 2 and 3 and control 15 a B8 allele (B*0801) is found. Samples 16 to 19 are homozygous controls for B35, B55, B56 and B54 respectively. In the negative controls (13 and 14 harbouring respectively the B*3701 and B*1801 alleles) no band could be observed. These alleles have the 5'-TCCG-3' sequence at position 30 to 33 of exon 2 instead of 5'-GCCA-3' (Zemmour and Parham, 1992).

Example 2

Dot Blot Typing Assay for Detection of the B78 Allele(s)

In this example the specific typing of the B*7801 allele is described making use of probes 6 and 17 (SEQ ID NO 12 and 23). Since B*7801 is the only allele hybridizing with both probes (6 and 17), B*7801 can be discriminated from the other alleles amplified with primer set B25P/B23P1.

The sequence-specific oligonucleotide-probes (SSOs) were chemically synthesized and labelled at their 3' end with digoxigenin-11-2'3'-dideoxy-uridine-5'-triphosphate (DIG-11-ddUTP) and DNA deoxynucleotidylexotransferase. Thirteen samples and 7 controls were amplified with primerset B25P/B23P1 as described in example 1.

Consequently 2 µl of PCR products were dot blotted onto nylon membranes (Hybond N Plus, Amersham, Buckinghamshire, UK) denatured by soaking the filters in 0.4N NaOH for 5 min and neutralized in 10 ml 10× SSPE (saline sodium phosphate EDTA) for 15 min. After blotting, membranes were prehybridized at 54° C. for 30 min in 10 ml of hybridization solution containing 50 mM Tris-HCl, (pH 8.0), 0.1% SDS, 2 mM EDTA, 3M TMAC (tetramethylammonium chloride, Janssen Chimica, Geel, Belgium). For hybridization, 3 pmol/ml DIG-labelled SSO were added to the prehybridization solution for 1 hour at 54° C., except for SSO-6 (SEQ ID NO 12) (52° C.). To remove probe excess, the filters were washed twice in (2× SSPE, 0.1% SDS) at room temperature for 10 min and then in hybridization solution for 15 min at the stringent temperature 58° C., except for the SSO-6 which was washed at 54° C.

The non-isotopic detection was performed using anti-DIG alkaline phosphatase, Fab fragments (anti-DIG-AP) and vizualization was obtained with the chemiluminescent substate AMPPD (3-(2'-spiroadamantane)-4 methoxy-4-(3"-phosphoryloxy)-phenyl-1,2-dioxetane). The drained membranes were exposed to an X-ray film (X-omat AR5, Kodak) in a cassette for 15–30 min. All reagents used in this oligotyping procedure were purchased form Boerhinger, Mannheim GmH, FRG. The results are illustrated in FIG. 3. All samples in which an allele of the B78 type is present (BSNA, BX1 or BTe76) clearly hybridize with probes 6 and 17 (SEQ ID NO 12 and 23). Other samples (n* 2, 3, 7, 15, 16, 17, 18, and 19) either hybridize with probe 17 (SEQ ID NO 23) or probe 6 (SEQ ID NO 12) but not with both. Since samples 13 and 14 are not amplified with the primerset used, hybridization signals are observed with neither probe 6 (SEQ ID NO 12) nor probe 17 (SEQ ID NO 23).

Example 3

Typing and Subtyping of B70 Variants

In this example the typing and subtyping of B70 variants is illustrated using 7 samples harbouring B70 variants. Also a blank and 7 non-B70 samples were included as controls (see table 3). B71 and B72 are alleles subtypic to the broad antigen HLA-B70. The sequence of the B72 allele (B*1503) is published (Zemmour and Parham, 1992); up to recently the B71 sequence was not. No monospecific B71 and B72 reagents are described and the presence of other antigens, most prominently B35 and B62, obscure exact serological assignment of the B70 variants. Distinction between B70 variants can be made by isoelectric focusing, but this is not a favourable technique in a routine setting.

By using the primer set B25P/B23P1 (SEQ ID NO 1 and 4) and a combination of some probes of the invention the B72 variants could be distinguished from other B70 variants. Here it should be emphasized that other variants than B71 and B72, as yet unidentified, might exist.

From a set of samples, known to harbour B70 variant alleles (samples 1 to 6 and 8, in table 3) DNA was extracted and amplified as described in example 1. The amplified products were applied to 5 nylon membranes which were further processed as described in example 2. These membranes were hybridizied respectively with the following sets of probes: 2, 6, 12, 13 and 15 (SEQ ID NO 8, 12, 18, 19 and 21). The results obtained with these probes are shown in FIG. 4. These results are summarized in table 3. In all cases the B72 variant (B*1503), which was present in 4 of the 7 B70 samples, could be distinguished from B71 or other possible variants. B*1503 (B72) is characterized by hybriding with probes 2 and 13 (SEQ ID NO 8 and 19) while other B70 variants were found to be non-reactive with probe 13 (SEQ ID NO 19). This example, thus, clearly illustrates the possibility to discriminate between alleles even when the sequence-information is not available.

Example 4

Typing of B46 Variants

Two B46 containing samples were typed using the same methods, primerset, and probe combination as discribed in example 3. In FIG. 4 and table 3 the typing results are given. By virtue of the presence of probe 12 (SEQ ID NO 18) in the probe panel, B*4601 can be easily traced and unequivocally distinguished from other alleles. From all alleles amplified by the primer set B25P/B23P1 (SEQ ID NO 1/4), B*4601 is the only allele hybridizing with probe 12 (SEQ ID NO 18).

Example 5

Line Probe Assay (LiPA) and SSO's for Typing of HLA-B Alleles

The prefered hybridization and wash- media for the Line Probe Assay (LiPA) are SSPE-based buffer solutions. LiPA strips were prepared essentially as described by Stuyver et al. (J. Gen. Virol. 74: 1093–1102, 1993). Since in a LiPA format all probes should react specifically under the same hybridization- and wash conditions (the same salt concentration and temperature) and the thermal melting point of DNA: DNA-hybrid in SSPE depends on the GC-content and lenght of the probe, modification of the probes listed in Table 2 is required for some probes to shift from a TMAC based buffer system to a SSPE based buffer system.

In order to select the most fitting probes to be used in a LiPA format a multitude of probes (listed in Table 2 bis) were synthesized, tailed at their 3' extremities using TTP and terminal transferase and immobilised on a solid support (nitrocellulose membrane). These probes were hybridised with target material using the following hybridization and wash conditions:

hybridization: −5×SSPE/0.5% SDS −55° C.
wash: −2×SSPE/0.1% SDS −55° C.
(1×SSPE is 0.18M NaCl, 0.01M $NaH_2PO_4$, 1 mM EDTA (pH 7.2))

The probes exhibiting the best test results with respect to specificity and sensitivity under the above mentioned conditions were selected for further use on the LiPA-strips. These probes were scored as positive (+) in Table 2 bis. Only 9 of the 20 probes used in the TMAC buffer system (SEQ ID NO 7b, 11, 12, 13, 18, 19, 21, 23 and 24) could be used without modification in the SSPE-based system.

These results clearly demonstrate that slight modifications of the sequence of the probes used might be of relevance and that meticulous probe design is essential for the development of a reliable LiPA-test.

Example 6

Typing of More Representative Homozygous Cell-lines Using the LiPA Strips

Due to co-amplification of the HLA-AR pseudogene (when primer B23P2 is used) hybridization results with probes 7 (SEQ ID NO 13) and 9 (SEQ ID NO. 15) are equivocal since sequences corresponding to those of probe 7 (SEQ ID NO 13) and 9 (SEQ ID NO 15) are present in the pseudogene.

In order to probe the origin of an eventual positive hybridization signal an additional amplification was performed using at least one of the B23 primers and a primer with the following sequence:

5'-GACGACACG/CCT/AGTTCGTGA-3' B25PX1(SEQ ID NO 53)

The amplification product obtained was consequently hybridized with a strip onto which at least probe 7 and 9 were immobilized.

A positive hybridization signal for probes 7 and 9 in this assay indicates that probe 7 and/or 9 sequences are present in the HLA-B alleles of the sample analysed and hence probes 7 and/or 9 should be scored positive. A negative result means that these probes should be neglected during the interpretation of the results after the first amplification since their positive hybridization signal originated from the pseudogene and not from the HLA-B gene itself.

Hybridization results obtained with some selected samples (homozygons cell-lines A to G) after separate amplification with primers B25P and B23PI/B23P2 (amplification 1) and with primers B25PX1 and B23P1/B23P2 (amplification 2) are summarized in Table 4. These results show that for sample A the positive hybridization signal for probes 7 and 9 originate from the HLA-B allele. The same is true for the positive signal obtained with probe 9 in samples E and F.

If the results after amplification steps 1 and 2 are combined, the following HLA-B alleles can be deduced with the aid of Table 1:

| sample | allele |
|--------|--------|
| A | B*0801 |
| B | B*1501 |
| C | B*4001 |
| D | B*4601 |
| E | B*5101 |
| F | B*5301 |
| G | B*5701 |

Essentially the same results are obtained when, for amplification 2, the following primer set is used:

B25P and B23P1/B23P3

TABLE 1

| ALLELES | 3'-PRIMER | | | PROBE | | | | | | |
|---------|-----------|-------|-------|---|---|---|---|---|---|---|
|         | B23P1 | B23P2 | B23P3 | 1 | 2 | 3 | 4 | 5 | 6 | 7 |
| 4001/4501/5001 | + | | + | + | | | | | | |
| 4901 | | + | + | + | | | | | | |
| 4101 | + | | + | + | | | | | | |
| 4701 | | | + | + | | | | | | |
| 1301/1302 | | + | + | + | | | | + | | |

TABLE 1-continued

| | | | | | | | | |
|---|---|---|---|---|---|---|---|---|
| 4401 to 4403 | | + | | + | + | | | |
| 0801 | + | | | | + | | | + |
| 5401 | + | | | | | + | | |
| 5501/5502/5601/5602 | + | | | | | + | | |
| 3501 to 3506 | + | | | | | + | + | |
| 5301 | | + | + | | | + | + | |
| 5101 to 5104 | | + | + | | + | | + | |
| 5201 | | + | + | | | + | | |
| 52012 | | + | + | | + | | + | |
| 7801 | + | | | | + | | + | |
| 1501/1504 | + | | + | | | + | + | |
| 1502 | + | | + | | | + | + | |
| 1503 | + | | + | + | | | + | |
| 4601 | + | | | | | + | + | |
| 7901 | + | | | + | + | | | + |
| 5701/5702 | | + | + | | | + | + | |
| 5801 | | + | + | | | + | + | |

| | PROBE | | | | | | | | | | | | |
|---|---|---|---|---|---|---|---|---|---|---|---|---|---|
| | 8 | 9 | 10 | 11 | 12 | 13 | 14 | 15 | 16 | 17 | 18 | 19 | 7b |
| 4001/4501/5001 | | + | | + | | | | | | + | + | + | |
| 4901 | | | + | | + | | | | | + | + | | |
| 4101 | | | + | | + | | | | | + | + | + | |
| 4701 | | | + | | + | | | | | + | + | | |
| 1301/1302 | | | + | | + | | | | | + | | | |
| 4401 to 4403 | | | + | | + | | | | | + | | + | |
| 0801 | | + | | | | + | | | + | + | | | |
| 5401 | + | + | | | | | + | | + | + | | | |
| 5501/5502/5601/5602 | | + | | | | | | + | + | + | | | |
| 3501 to 3506 | | + | | | | + | | | | + | + | | |
| 5301 | | + | | | | + | | | + | | | | |
| 5101 to 5104 | | + | | | | + | | | + | | | | |
| 5201 | | | + | | + | | | | + | | | | |
| 52012 | | | + | | + | | | | + | | | | |
| 7801 | + | | | | + | | | | + | | | | |
| 1501/1504 | | | + | | + | | | | | + | + | | |
| 1502 | + | | | | + | | | | | + | | | |
| 1503 | | + | | + | | | | | | + | + | | |
| 4601 | | + | + | | | | | | | | | | |
| 7901 | + | | | | | | | + | | + | + | | |
| 5701/5702 | | + | | | | | | | | | | | |
| 5801 | | + | | | | | | | | | | | |

TABLE 2

Oligonucleotide probe DNA sequences

| | | |
|---|---|---|
| 1 | 5'-GCTTCATCACCGTGGGCT-3' | (SEQ ID NO 7) |
| 2 | 5'-CGCTTCATCTCAGTGGGC-3' | (SEQ ID NO 8) |
| 3 | 5'-CGCTTCATTGCAGTGGGC-3' | (SEQ ID NO 9) |
| 4 | 5'-CGCTTCATCGCAGTGGGC-3' | (SEQ ID NO 10) |
| 5 | 5'-CCGAGGATGGCGCCCCGG-3' | (SEQ ID NO 11) |
| 6 | 5'-TCCGAGGACGGAGCCCCG-3' | (SEQ ID NO 12) |
| 7 | 5'-AGTCCGAGAGAGGAGCCG-3' | (SEQ ID NO 13) |
| 7b | 5'-GTCCGAGGAAGGAGCCGC-3' | (SEQ ID NO 26) |
| 8 | 5'-GCGCCGTGGGTGGAGCAG-3' | (SEQ ID NO 14) |
| 9 | 5'-GGGACCGGAACACACAGA-3' | (SEQ ID NO 15) |
| 10 | 5'-GGACCGGGAGACACAGAT-3' | (SEQ ID NO 16) |
| 11 | 5'-GGACGGGGAGACACGGAA-3' | (SEQ ID NO 17) |
| 12 | 5'-ACACAGAAGTACAAGCGC-3' | (SEQ ID NO 18) |
| 13 | 5'-CAGATCTCCAAGACCAAC-3' | (SEQ ID NO 19) |

TABLE 2-continued

Oligonucleotide probe DNA sequences

| | | |
|---|---|---|
| 14 | 5'-ACAGATCTTCAAGACCAA-3' | (SEQ ID NO 20) |
| 15 | 5'-CAGATCTACAAGGCCCAG-3' | (SEQ ID NO 21) |
| 16 | 5'-ACAGATCTGCAAGACCAA-3' | (SEQ ID NO 22) |
| 17 | 5'-ACAGACTGACCGAGAGAG-3' | (SEQ ID NO 23) |
| 18 | 5'-CACAGACTTACCGAGAGA-3' | (SEQ ID NO 24) |
| 19 | 5'-ACCGAGAGAGCCTGCGGA-3' | (SEQ ID NO 25) |

TABLE 2b

| | | | |
|---|---|---|---|
| S01 | + | 5'-CTTCATCACCGTGGGCT-3' | (SEQ ID NO 27) |
| S02 | + | 5'-GCTTCATCTCAGTGGGC-3' | (SEQ ID NO 28) |
| S03 | + | 5'-GCTTCATTGCAGTGGGC-3' | (SEQ ID NO 29) |
| S04 | + | 5'-CTTCATCGCAGTGGGC-3' | (SEQ ID NO 30) |
| S05 | | 5'-GATGGCGCCCCGG-3' | (SEQ ID NO 31) |
| S05(2) | | 5'-GAGGATGGCGCCCCGG-3' | (SEQ ID NO 32) |
| S05(3) | + | 5'-CCGAGGATGGCGCCCCGG-3' | (SEQ ID NO 11) |
| S06 | | 5'-GGACCGGAGCCCCG-3' | (SEQ ID NO 33) |
| S06(2) | | 5'-CGAGGACGGAGCCCCG-3' | (SEQ ID NO 34) |
| S06(3) | | 5'-CCGAGGACGGAGCCCCG-3' | (SEQ ID NO 35) |
| S06(4) | | 5'-TCCGAGGACGGAGCCCCG-3' | (SEQ ID NO 12) |
| S06(5) | + | 5'-TCCGAGGACGGAGCCCCGG-3' | (SEQ ID NO 36) |
| S07 | | 5'-TCCGAGAGAGGAGCC-3' | (SEQ ID NO 37) |
| S07(2) | | 5'-AGTCCGAGAGAGGAGCC-3' | (SEQ ID NO 38) |
| S07(3) | + | 5'-AGTCCGAGAGAGGAGCCG-3' | (SEQ ID NO 13) |
| S07b | + | 5'-GTCCGAGGAAGGAGCCGC-3' | (SEQ ID NO 26) |
| S08 | + | 5'-CCGTGGGTGGAGCAG-3' | (SEQ ID NO 39) |
| S08(2) | | 5'-CGCCGTGGGTGGAGCAG-3' | (SEQ ID NO 40) |
| S09 | | 5'-GGACCGGAACACACAGA-3' | (SEQ ID NO 41) |
| S09(2) | | 5'-GACCGGAACACACAGA-3' | (SEQ ID NO 42) |
| S09(3) | | 5'-GACCGGAACACACAG-3' | (SEQ ID NO 43) |
| S09(4) | + | 5'-GGACCGGAACACACAG-3' | (SEQ ID NO 44) |
| S10 | + | 5'-GACCGGGAGACACAGAT-3' | (SEQ ID NO 45) |
| S11 | + | 5'-ACGGGGAGACACGGAA-3' | (SEQ ID NO 46) |
| S12 | + | 5'-ACACAGAAGTACAAGCGC-3' | (SEQ ID NO 18) |
| S13 | + | 5'-CAGATCTCCAAGACCAAC-3' | (SEQ ID NO 19) |
| S14 | | 5'-CACAGATCTTCAAGACCAAC-3' | (SEQ ID NO 47) |
| S14(2) | | 5'-ACAGATCTTCAAGACCAAC-3' | (SEQ ID NO 48) |
| S14(3) | + | 5'-CAGATCTTCAAGACCAA-3' | (SEQ ID NO 49) |
| S15 | + | 5'-CAGATCTACAAGGCCCAG-3' | (SEQ ID NO 21) |
| S16 | + | 5'-CACAGATCTGCAAGACCAA-3' | (SEQ ID NO 50) |
| S17 | + | 5'-ACAGACTGACCGAGAGAG-3' | (SEQ ID NO 23) |
| S18 | + | 5'-CACAGACTTACCGAGAGA-3' | (SEQ ID NO 24) |
| S19 | + | 5'-CGAGAGAGCCTGCGG-3' | (SEQ ID NO 51) |
| S19(2) | + | 5'-CGAGAGAGCCTGCGGA-3' | (SEQ ID NO 52) |

TABLE 3

| | PROBE | | | | | |
|---|---|---|---|---|---|---|
| SAMPLE | 2 | 12 | 15 | 6 | 13 | B70 or B46 allele identified |
| 1 B70/B78 | + | | | + | + | B*1503 |
| 2 B51/B70 | + | | | | | B70 (B71?) |
| 3 B49/B71 | + | | | | | B70 (B71?) |
| 4 B07/B72 | + | | | | + | B*1503 |
| 5 B49/B72 | + | | | | + | B*1503 |
| 6 B07/B72 | + | | | | + | B*1503 |
| 7 B07/B49 | | | | | | — |
| 8 ?/B70 | + | | | | | B70 (B71?) |
| 9 blank | | | | | | — |
| 10 B75/B46 | | | | + | | B*4601 |
| 11 B46/B46 | | | | + | | B*4601 |
| 12 B51/B35 | | | | | + | — |
| 13 B08/B35 | + | | | | | — |
| 14 B08/B44 | | | | | + | — |
| 15 B44/B44 | | | | | | — |

TABLE 4

| Samples | Amplification 1 | | | | | | | | | | | | | | | | | | | Amplification 2 | |
|---|---|---|---|---|---|---|---|---|---|---|---|---|---|---|---|---|---|---|---|---|---|
| | 1 | 2 | 3 | 4 | 5 | 6 | 7 | 7b | 8 | 9 | 10 | 11 | 12 | 13 | 14 | 15 | 16 | 17 | 18 | 19 | 7 | 9 |
| A | | + | | | | | + | | | + | | | | | + | | | + | + | + | + | + |
| B | | | | + | + | | + | | | + | + | | | + | | | | + | + | | | |
| C | + | | | | | | | + | | + | + | | | + | | | | + | + | | | |
| D | | | | + | + | | | | | + | + | | + | | | | | | | | | |
| E | | | + | | | + | + | | | + | | | | | + | | | + | | | | + |
| F | | | | + | | + | + | | | + | | | | | + | | | + | | | | + |
| G | | | | + | + | | | | | + | + | | + | | | | | | | | | |

---

We claim:

1. A solid support carrying on its surface at least one probe selected from SEQ ID NO:s 7–26.

2. The solid support according to claim 1, said solid support carrying on its surface two probes, said support being a membrane strip and said probes being arranged on said strip in parallel lines.

3. A composition comprising at least one of the amplification primers selected from 5'-AGGTATTTCTACACCGCCA-3' (B25P, SEQ ID NO: 1), 5'-AGGTATTTCCACACCGCCA-3'(SEQ ID NO:2), and 5'-AGGTATTTCGACACCGCCA-3' (SEQ ID NO:3), and optionally, at least one of the oligonucleotide amplification primers selected from the list 5'-TCTGGTTGTAGTAGCCGCGCA-3' (B23P1, SEQ ID NO:4), 5'-TCTGGTTGTAGTAGCGGAGCG-3' (B23P2, SEQ ID NO:5), 5'-TCCGCAGGTTCTCTCGGTA-3' (B23P3, SEQ ID NO:6).

4. A composition comprising at least one oligonucleotide probe selected from SEQ ID NO:s 7–52.

* * * * *

SEQUENCE LISTING ( 1 ) GENERAL INFORMATION:

( i i i ) NUMBER OF SEQUENCES: 53

( 2 ) INFORMATION FOR SEQ ID NO: 1:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Primer B25P
        ( B ) LOCATION: anneals to nucleotides 15-33 of exon 2 of e.g.
            HLA-B*3501

( x i ) SEQUENCE DESCRIPTION: SEQ ID NO: 1:

AGGTATTTCT ACACCGCCA                                                                19

( 2 ) INFORMATION FOR SEQ ID NO: 2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Primer B25P variant
        ( B ) LOCATION: anneals to nucleotides 15-33 of exon 2 of e.g.
            HLA-B*4001

( x i ) SEQUENCE DESCRIPTION: SEQ ID NO: 2:

AGGTATTTCC ACACCGCCA                                                                19

( 2 ) INFORMATION FOR SEQ ID NO: 3:

( i ) SEQUENCE CHARACTERISTICS:
        ( A ) LENGTH: 19 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iii) ANTI-SENSE: NO (ix) FEATURE:
 (A) NAME/KEY: Oligonucleotide Primer B25P variant
 (B) LOCATION: anneals to nucleotides 15-33 of exon 2 of
  HLA-B*0801

(xi) SEQUENCE DESCRIPTION: SEQ ID NO: 3:

AGGTATTTCG ACACCGCCA   19

(2) INFORMATION FOR SEQ ID NO: 4:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iii) ANTI-SENSE: YES (ix) FEATURE:
  (A) NAME/KEY: Oligonucleotide Primer B23P1
  (B) LOCATION: anneals to nucleotides 241-261 of exon 2 of e.g.
   HLA-B*4001

(xi) SEQUENCE DESCRIPTION: SEQ ID NO: 4:

TCTGGTTGTA GTAGCCGCGC A   21

(2) INFORMATION FOR SEQ ID NO: 5:

(i) SEQUENCE CHARACTERISTICS:
  (A) LENGTH: 21 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iii) ANTI-SENSE: YES (ix) FEATURE:
  (A) NAME/KEY: Oligonucleotide Primer B23P2
  (B) LOCATION: anneals to nucleotides 241-261 of exon 2 of e.g.
   HLA-B*1301

(xi) SEQUENCE DESCRIPTION: SEQ ID NO: 5:

TCTGGTTGTA GTAGCGGAGC G   21

(2) INFORMATION FOR SEQ ID NO: 6:

(i) SEQUENCE CHARACTERISTICS:
  (A) LENGTH: 19 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iii) ANTI-SENSE: YES ( i x ) FEATURE:
	( A ) NAME/KEY: Oligonucleotide Primer B23P3
	( B ) LOCATION: anneals to nucleotides 219-237 of exon 2 of e.g. HLA-B*5101

( x i ) SEQUENCE DESCRIPTION: SEQ ID NO: 6:

TCCGCAGGTT CTCTCGGTA                                                                                            19

( 2 ) INFORMATION FOR SEQ ID NO: 7:

( i ) SEQUENCE CHARACTERISTICS:
		( A ) LENGTH: 18 base pairs
		( B ) TYPE: nucleic acid
		( C ) STRANDEDNESS: single
		( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
		( A ) NAME/KEY: Oligonucleotide Probe 1
		( B ) LOCATION: anneals to nucleotides 61-78 of exon 2 of e.g. HLA-B*4001

( x i ) SEQUENCE DESCRIPTION: SEQ ID NO: 7:

GCTTCATCAC CGTGGGCT                                                                                             18

( 2 ) INFORMATION FOR SEQ ID NO: 8:

( i ) SEQUENCE CHARACTERISTICS:
		( A ) LENGTH: 18 base pairs
		( B ) TYPE: nucleic acid
		( C ) STRANDEDNESS: single
		( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
		( A ) NAME/KEY: Oligonucleotide Probe 2
		( B ) LOCATION: anneals to nucleotides 60-77 of exon 2 of e.g. HLA-B*0801

( x i ) SEQUENCE DESCRIPTION: SEQ ID NO: 8:

CGCTTCATCT CAGTGGGC                                                                                             18

( 2 ) INFORMATION FOR SEQ ID NO: 9:

( i ) SEQUENCE CHARACTERISTICS:
		( A ) LENGTH: 18 base pairs
		( B ) TYPE: nucleic acid
		( C ) STRANDEDNESS: single
		( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
		( A ) NAME/KEY: Oligonucleotide Probe 3
		( B ) LOCATION: anneals to nucleotides 60-77 of exon 2 of e.g. HLA-B*5101

( x i ) SEQUENCE DESCRIPTION: SEQ ID NO: 9:

CGCTTCATTG CAGTGGGC                                                                                             18

( 2 ) INFORMATION FOR SEQ ID NO: 10:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Probe 4
        ( B ) LOCATION: anneals to nucleotides 60-77 of exon 2 of e.g.
            HLA-B*3501

( x i ) SEQUENCE DESCRIPTION: SEQ ID NO: 10:

CGCTTCATCG CAGTGGGC                                                                            18

( 2 ) INFORMATION FOR SEQ ID NO: 11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Probe 5
        ( B ) LOCATION: anneals to nucleotides 126-143 of exon 2 of e.g.
            HLA-B*1501

( x i ) SEQUENCE DESCRIPTION: SEQ ID NO: 11:

CCGAGGATGG CGCCCCGG                                                                            18

( 2 ) INFORMATION FOR SEQ ID NO: 12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Probe 6
        ( B ) LOCATION: anneals to nucleotides 125-142 of exon 2 of e.g.
            HLA-B*3501

( x i ) SEQUENCE DESCRIPTION: SEQ ID NO: 12:

TCCGAGGACG GAGCCCCG                                                                            18

( 2 ) INFORMATION FOR SEQ ID NO: 13:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (ii) MOLECULE TYPE: DNA (genomic)

(iii) HYPOTHETICAL: NO (iii) ANTI-SENSE: NO (ix) FEATURE:
 (A) NAME/KEY: Oligonucleotide Probe 7
 (B) LOCATION: anneals to nucleotides 123-140 of exon 2 of e.g.
  HLA-B*0801

(xi) SEQUENCE DESCRIPTION: SEQ ID NO: 13:

AGTCCGAGAG AGGAGCCG 18

(2) INFORMATION FOR SEQ ID NO: 14:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iii) ANTI-SENSE: NO (ix) FEATURE:
  (A) NAME/KEY: Oligonucleotide Probe 8
  (B) LOCATION: anneals to nucleotides 143-161 of exon 2 of e.g.
   HLA-B*5401

(xi) SEQUENCE DESCRIPTION: SEQ ID NO: 14:

GCGCCGTGGG TGGAGCAG 18

(2) INFORMATION FOR SEQ ID NO: 15:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iii) ANTI-SENSE: NO (ix) FEATURE:
  (A) NAME/KEY: Oligonucleotide Probe 9
  (B) LOCATION: anneals to nucleotides 178-195 of exon 2 of e.g.
   HLA-B*0801

(xi) SEQUENCE DESCRIPTION: SEQ ID NO: 15:

GGGACCGGAA CACACAGA 18

(2) INFORMATION FOR SEQ ID NO: 16:

(i) SEQUENCE CHARACTERISTICS:
  (A) LENGTH: 18 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iii) ANTI-SENSE: NO ( i x ) FEATURE:
    ( A ) NAME/KEY: Oligonucleotide Probe 10
    ( B ) LOCATION: anneals to nucleotides 179-196 of exon 2 of e.g.
        HLA-B*4001

( x i ) SEQUENCE DESCRIPTION: SEQ ID NO: 16:

GGACCGGGAG ACACAGAT 18

( 2 ) INFORMATION FOR SEQ ID NO: 17:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
    ( A ) NAME/KEY: Oligonucleotide Probe 11
    ( B ) LOCATION: anneals to nucleotides 179-196 of exon 2 of e.g.
        HLA-B*5701

( x i ) SEQUENCE DESCRIPTION: SEQ ID NO: 17:

GGACGGGGAG ACACGGAA 18

( 2 ) INFORMATION FOR SEQ ID NO: 18:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
    ( A ) NAME/KEY: Oligonucleotide Probe 12
    ( B ) LOCATION: anneals to nucleotides 189-206 of exon 2 of
        HLA-B*4601

( x i ) SEQUENCE DESCRIPTION: SEQ ID NO: 18:

ACACAGAAGT ACAAGCGC 18

( 2 ) INFORMATION FOR SEQ ID NO: 19:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
    ( A ) NAME/KEY: Oligonucleotide Probe 13
    ( B ) LOCATION: anneals to nucleotides 192-209 of exon 2 of
        HLA-B*4001

( x i ) SEQUENCE DESCRIPTION: SEQ ID NO: 19:

CAGATCTCCA AGACCAAC 18

( 2 ) INFORMATION FOR SEQ ID NO: 20:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Probe 14
        ( B ) LOCATION: anneals to nucleotides 191-208 of exon 2 of e.g. HLA-B*0801

( x i ) SEQUENCE DESCRIPTION: SEQ ID NO: 20:

ACAGATCTTC AAGACCAA      18

( 2 ) INFORMATION FOR SEQ ID NO: 21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Probe 15
        ( B ) LOCATION: anneals to nucleotides 192-209 of exon 2 of e.g. HLA-B*5401

( x i ) SEQUENCE DESCRIPTION: SEQ ID NO: 21:

CAGATCTACA AGGCCCAG      18

( 2 ) INFORMATION FOR SEQ ID NO: 22:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( i x ) FEATURE:
        ( A ) NAME/KEY: Oligonucleotide Probe 16
        ( B ) LOCATION: anneals to nucleotides 191-208 of exon 2 of e.g. HLA-B*7901

( x i ) SEQUENCE DESCRIPTION: SEQ ID NO: 22:

ACAGATCTGC AAGACCAA      18

( 2 ) INFORMATION FOR SEQ ID NO: 23:

( i ) SEQUENCE CHARACTERISTICS:
        ( A ) LENGTH: 18 base pairs
        ( B ) TYPE: nucleic acid
        ( C ) STRANDEDNESS: single (D) TOPOLOGY: linear (i i) MOLECULE TYPE: DNA (genomic)

(i i i) HYPOTHETICAL: NO (i i i) ANTI-SENSE: NO (i x) FEATURE:
    (A) NAME/KEY: Oligonucleotide Probe 17
    (B) LOCATION: anneals to nucleotides 212-229 of exon 2 of e.g.
        HLA-B*7801

(x i) SEQUENCE DESCRIPTION: SEQ ID NO: 23:

ACAGACTGAC CGAGAGAG      18

(2) INFORMATION FOR SEQ ID NO: 24:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i i i) ANTI-SENSE: NO (i x) FEATURE:
    (A) NAME/KEY: Oligonucleotide Probe 18
    (B) LOCATION: anneals to nucleotides 211-228 of exon 2 of e.g.
        HLA-B*4001

(x i) SEQUENCE DESCRIPTION: SEQ ID NO: 24:

CACAGACTTA CCGAGAGA      18

(2) INFORMATION FOR SEQ ID NO: 25:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i i i) ANTI-SENSE: NO (i x) FEATURE:
    (A) NAME/KEY: Oligonucleotide Probe 19
    (B) LOCATION: anneals to nucleotides 220-237 of exon 2 of e.g.
        HLA-B*4001

(x i) SEQUENCE DESCRIPTION: SEQ ID NO: 25:

ACCGAGAGAG CCTGCGGA      18

(2) INFORMATION FOR SEQ ID NO: 26:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (i i) MOLECULE TYPE: DNA (genomic)

(i i i) HYPOTHETICAL: NO (i i i) ANTI-SENSE: NO ( x i ) SEQUENCE DESCRIPTION: SEQ ID NO: 26:

GTCCGAGGAA GGAGCCGC                                                                                                       18

( 2 ) INFORMATION FOR SEQ ID NO: 27:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 27:

CTTCATCACC GTGGGCT                                                                                                        17

( 2 ) INFORMATION FOR SEQ ID NO: 28:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 28:

GCTTCATCTC AGTGGGC                                                                                                        17

( 2 ) INFORMATION FOR SEQ ID NO: 29:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 29:

GCTTCATTGC AGTGGGC                                                                                                        17

( 2 ) INFORMATION FOR SEQ ID NO: 30:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 30:

CTTCATCGCA GTGGGC                                                                                                         16

( 2 ) INFORMATION FOR SEQ ID NO: 31:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 31:

GATGGCGCCC CGG 13

( 2 ) INFORMATION FOR SEQ ID NO: 32:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 32:

GGACGGAGCC CCG 13

( 2 ) INFORMATION FOR SEQ ID NO: 33:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 33:

GAGGATGGCG CCCCGG 16

( 2 ) INFORMATION FOR SEQ ID NO: 34:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 34:

CGAGGACGGA GCCCCG 16

( 2 ) INFORMATION FOR SEQ ID NO: 35:

( i ) SEQUENCE CHARACTERISTICS:

(A) LENGTH: 17 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 35:

CCGAGGACGG AGCCCCG 17

(2) INFORMATION FOR SEQ ID NO: 36:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 36:

TCCGAGGACG GAGCCCCGG 19

(2) INFORMATION FOR SEQ ID NO: 37:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 37:

TCCGAGAGAG GAGCC 15

(2) INFORMATION FOR SEQ ID NO: 38:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 38:

AGTCCGAGAG AGGAGCC 17

(2) INFORMATION FOR SEQ ID NO: 39:

(i) SEQUENCE CHARACTERISTICS:
(A) LENGTH: 15 base pairs
(B) TYPE: nucleic acid
(C) STRANDEDNESS: single
(D) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 39:

CCGTGGGTGG AGCAG 15

( 2 ) INFORMATION FOR SEQ ID NO: 40:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 40:

CGCCGTGGGT GGAGCAG 17

( 2 ) INFORMATION FOR SEQ ID NO: 41:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 41:

GGACCGGAAC ACACAGA 17

( 2 ) INFORMATION FOR SEQ ID NO: 42:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 42:

GACCGGAACA CACAGA 16

( 2 ) INFORMATION FOR SEQ ID NO: 43:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 43:

GACCGGAACA CACAG                                                                                                        15

( 2 ) INFORMATION FOR SEQ ID NO: 44:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 44:

GGACCGGAAC ACACAG                                                                                                       16

( 2 ) INFORMATION FOR SEQ ID NO: 45:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 45:

GACCGGGAGA CACAGAT                                                                                                      17

( 2 ) INFORMATION FOR SEQ ID NO: 46:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 46:

ACGGGGAGAC ACGGAA                                                                                                       16

( 2 ) INFORMATION FOR SEQ ID NO: 47:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 47:

CACAGATCTT CAAGACCAAC 20

( 2 ) INFORMATION FOR SEQ ID NO: 48:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 48:

ACAGATCTTC AAGACCAAC 19

( 2 ) INFORMATION FOR SEQ ID NO: 49:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 49:

CAGATCTTCA AGACCAA 17

( 2 ) INFORMATION FOR SEQ ID NO: 50:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 50:

CACAGATCTG CAAGACCAA 19

( 2 ) INFORMATION FOR SEQ ID NO: 51:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i i i ) ANTI-SENSE: NO ( x i ) SEQUENCE DESCRIPTION: SEQ ID NO: 51:

CGAGAGAGCC TGCGG 15

(2) INFORMATION FOR SEQ ID NO: 52:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (xi) SEQUENCE DESCRIPTION: SEQ ID NO: 52:

CGAGAGAGCC TGCGGA     16

(2) INFORMATION FOR SEQ ID NO: 53:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (ix) FEATURE:
        (A) NAME/KEY: misc_feature
        (B) LOCATION: 9
        (D) OTHER INFORMATION: /standard_name= "G or C"

(ix) FEATURE:
        (A) NAME/KEY: misc_feature
        (B) LOCATION: 12
        (D) OTHER INFORMATION: /standard_name= "T or A"

(xi) SEQUENCE DESCRIPTION: SEQ ID NO: 53:

GACGACACSC CWGTTCGTGA     20